United States Patent [19]

Jess

[11] 4,155,362
[45] May 22, 1979

[54] METHOD AND APPARATUS FOR METERED INFUSION OF FLUIDS

[75] Inventor: Thurman S. Jess, Mundelein, Ill.

[73] Assignee: Baxter Travenol Laboratories, Inc., Deerfield, Ill.

[21] Appl. No.: 759,178

[22] Filed: Jan. 13, 1977

Related U.S. Application Data

[63] Continuation-in-part of Ser. No. 652,937, Jan. 26, 1976, abandoned.

[51] Int. Cl.² .............................................. A61M 5/00
[52] U.S. Cl. ......................... 128/214 F; 128/DIG. 12; 417/477
[58] Field of Search ........... 128/214 R, 214 B, 214 E, 128/214 F, 214.2, 230, 273, DIG. 12, DIG. 13; 417/474–477, 441; 251/7, 8

[56] References Cited

U.S. PATENT DOCUMENTS

| 2,366,424 | 1/1945 | Perry | 128/214 R |
| 2,393,838 | 1/1946 | Tarbox | 417/474 |
| 2,483,924 | 10/1949 | Moulinier | 128/214 F X |
| 3,620,650 | 11/1971 | Shaw | 417/476 X |
| 3,675,653 | 7/1972 | Crowley et al. | 128/278 |
| 3,726,613 | 4/1973 | Casimir | 417/477 |
| 3,731,680 | 5/1973 | Wright | 128/214 F |
| 3,990,444 | 11/1976 | Vial | 128/214 F |

FOREIGN PATENT DOCUMENTS 931304 7/1963 United Kingdom ..................... 417/477

OTHER PUBLICATIONS

Hannemann et al., Am. Jo. Dis. Child, vol. 125, May 1973, pp. 706–708.

*Primary Examiner*—Dalton L. Truluck
*Attorney, Agent, or Firm*—Paul C. Flattery; Eugene M. Cummings

[57] ABSTRACT

A method and apparatus for infusing fluids into the human body includes a peristaltic-type pump and an administration set having a vinyl tubing section on which the pump acts. To prevent the release of dissolved gas in the tubing section and the possible coalescence of released gas bubbles into pockets of air the pressure in the tubing downline of the pump is increased by partially restricting the lumen of the tubing. This restriction also assists in restoring the tubing to its original shape following compression by the peristaltic pump for more accurate metering and more efficient pumping action, and prevents uncontrolled gravity flow in the event of a pump failure. To provide a uniform compression force on the tubing the pressure rollers of the peristaltic pump are individually spring biased against the wall of the tubing, which is held in position by a stationary pressure plate.

29 Claims, 17 Drawing Figures

METHOD AND APPARATUS FOR METERED INFUSION OF FLUIDS

This application is a continuation-in-part of application Ser. No. 652,937, filed Jan. 26, 1976, now abandoned.

BACKGROUND OF THE INVENTION

The present invention relates to fluid infusion systems, and more particularly to an improved apparatus and method for infusing fluid into the human body.

The infusion of fluids such as parenteral solutions and blood into the human body is usually accomplished by means of an administration set in conjunction with appropriate flow metering means to control the rate of fluid flow through the set. One form of flow metering means which is potentially attractive for this application is the peristaltic-type pump, which operates to repeatedly compress and expand a section of tubing so as to cause fluid to flow through the tubing at a controlled rate. Unfortunately, the operation of such peristaltic-type pumps in connection with administration sets has not been entirely satisfactory because of metering inaccuracies brought about by the partially non-resilient characteristic of the vinyl tubing commonly used in such sets, and as a result the use of such pumps has been limited to applications requiring less critical flow rate control such as blood processing.

In the course of operation of a peristaltic pump the tubing on which the pump acts is subjected to repeated stretch-compression cycling. Because of its partial non-resiliency, tubing formed of vinyl and other thermoplastic materials may permanently change its shape and size with time as a result of such cycling, with the result that the rate at which fluid is delivered by the pump may be undesirably varied. Prior art peristaltic-type pumps have employed follower pins, rollers, pinchers, or similar means, to bear against the edges of the deformed tubing following compression to attempt to restore the tubing to its original shape, but these methods have had only limited success.

Another problem which arises with the use of peristaltic-type pumps in conjunction with fluid infusion sets is that should a failure of the tubing occur, or should the tubing be accidentally removed from the pump, the possibility of uncontrolled gravity flow of fluid into the body exists. Furthermore, dissolved gases in a liquid being infused may be released as bubbles as the liquid is subjected to pressure and/or temperature changes as it passes through the peristaltic pump. These bubbles may coalesce and form larger bubbles or pockets of gas which may be infused along with the liquid into the body, which may be harmful or even fatal to the patient under certain circumstances.

To prevent gas from being infused sensors may be located below the discharge end of the pump to automatically stop the pump should gas be detected or should the flow of fluid be interrupted. While such sensors are effective in preventing the infusion of gas, the stoppage of the infusion process they cause may itself be a risk to a critically ill patient, necessitating the continuous availability of medical personnel to re-establish the process.

The present invention is directed to a system for infusing fluid which provides improved fluid rate control by minimizing physical and dimensional changes in the tubing, minimizes the release of dissolved gases from the fluid, and guards against uncontrolled fluid flow should the pump fail or be inadvertently removed.

Prior art peristaltic pumps have typically included a plurality of rollers or the like against which the tubing is compressed by means of a spring-biased pressure plate so that as the rollers are advanced along the plate the tubing is repeatedly compressed and released to cause fluid to flow through the tubing. In such pumps, the number of rollers in compressive contact with the tubing varies as the rollers are advanced, so that, for example, at one point in time two rollers may compress the tubing, and at another time, one roller may compress the tubing. Since the rollers act on a common pressure plate, the compression force exerted on the tubing by any one roller varies as the number of rollers compressing the tubing varies. If the compression force varies too widely, for instance at a 2:1 ratio, the vinyl tubing commonly used in infusion sets may be caused to deform rapidly, stretch, extrude, and possibly even break open. The ultimate result could be a drop in or loss of fluid flow rate with possible harm to the patient.

The present invention is further directed to an improved peristaltic-type pump for use in conjunction with fluid infusion systems which provides a uniform compression force on an associated tubing segment, regardless of the number of points at which the tubing segment is being compressed.

Accordingly, it is a general object of the present invention to provide a new and improved fluid infusion system.

It is another object of the present invention to provide a new and improved system for infusing fluids into the human body which provides more accurate metering and improved pump efficiency.

It is another object of the present invention to provide a new and improved system for infusing fluids into the human body which provides improved protection against uncontrolled flow of fluid through the system.

It is another object of the present invention to provide a new and improved peristaltic pump which maintains a uniform compression force on an associated length of tubing regardless of the number of points at which the tubing is compressed.

SUMMARY OF THE INVENTION

The invention is directed to a flow system for infusing a fluid from a reservoir into the human body. The system includes a flexible tubing segment disposed between the reservoir and the body, a pump disposed along the tubing segment and coacting therewith to meter the liquid through the segment, and flow restriction means disposed downline of the pump for increasing the pressure of the liquid in the tubing whereby gas dissolved in the liquid is held in solution notwithstanding pressure and temperature changes brought about by the pump.

The invention is further directed, in a flow system for infusing a fluid from a reservoir into the human body, the system including a flexible tubing segment extending between the reservoir and the point of infusion, to a pump assembly comprising a pump disposed along the tubing segment and coacting therewith to meter the flow of liquid through the segment, and flow restriction means disposed downline of the pump for increasing the pressure of the liquid in the tubing whereby gas dissolved therein is maintained in solution notwithstanding pressure and/or temperature changes brought about by the pump.

The invention is further directed to a method for infusing a fluid from a liquid reservoir into the human body comprising the steps of establishing a flow path for the fluid from the reservoir to the body, urging the fluid along the flow path, and partially blocking the flow path downline of the pump and upline of the point of infusion into the body to increase the pressure of the fluid at the pump to maintain gases dissolved therein in solution.

The invention is further directed to a flow system for infusing a fluid from a reservoir into the human body wherein a flexible-walled tubing segment is disposed between the reservoir and the body, a peristaltic-type pump having at least one pressure member arranged for deforming the sidewall of the tubing segment at a first predetermined location thereon is provided to meter the flow of fluid through the segment, and flow restriction means are disposed at a second predetermined location downline of the first predetermined location for increasing the pressure of the fluid in the tubing between the first and second predetermined locations to assist the wall of the tubing segment in reforming following deformation by the pressure member.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

DESCRIPTION OF THE PREFERRED EMBODIMENT

Figure 1:
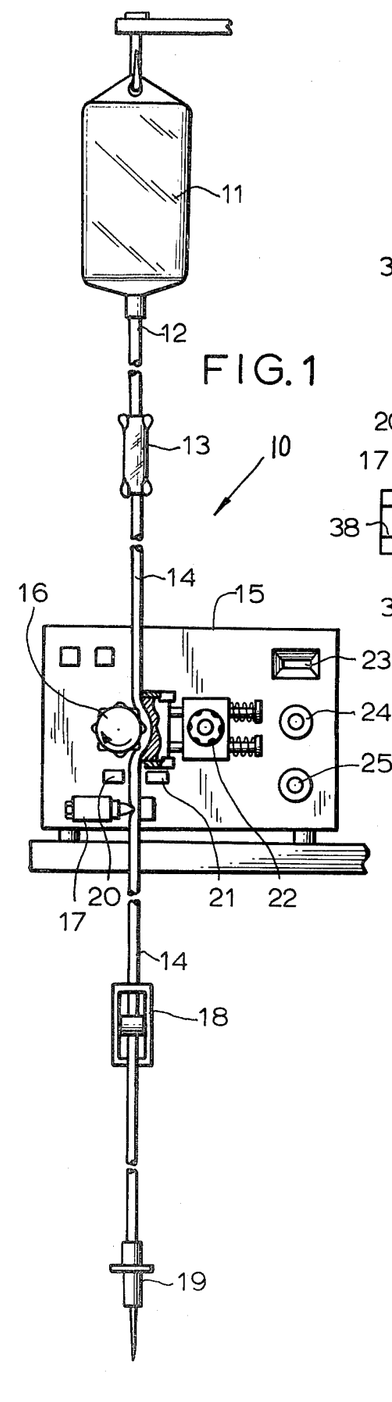
FIG. 1 is a perspective view of an infusion system constructed in accordance with the invention.

Referring to the Figures, and particularly to FIG. 1, an infusion system 10 constructed in accordance with the invention for injecting a fluid into a vein or artery from a reservoir 11 includes a disposable administration set consisting of a first tubing segment 12, a drip chamber 13, a second tubing segment 14, a flow control tubing clamp 18, and a needle adaptor 19 to which a needle of appropriate size and shape is attached. The tubing segments of the administration set, which may be conventional in design and construction and may be packaged in a sterile and non-pyrogenic condition, are preferably formed of a thermoplastic material such as vinyl.

The second tubing section 14 of the administration set passes through a pump assembly 15 which includes a rotary-type peristaltic pump 16 and a flow restriction station 17 downline of the pump. The pump assembly includes an appropriate mechanical linkage 22 for disengaging the tubing 14 from the pump and flow restriction station during assembly and disassembly. Appropriate pump control circuitry may also be provided to enable accurate and consistent control and metering of the fluid infused into the body. Such circuitry may include a photocell 21 and coacting light source 20 for detecting the absence of fluid in the tubing, a dosage counter 23 for totalizing fluid delivered and controls 24 and 25 for controlling delivery rate and total dosage, respectively.

Figure 2:
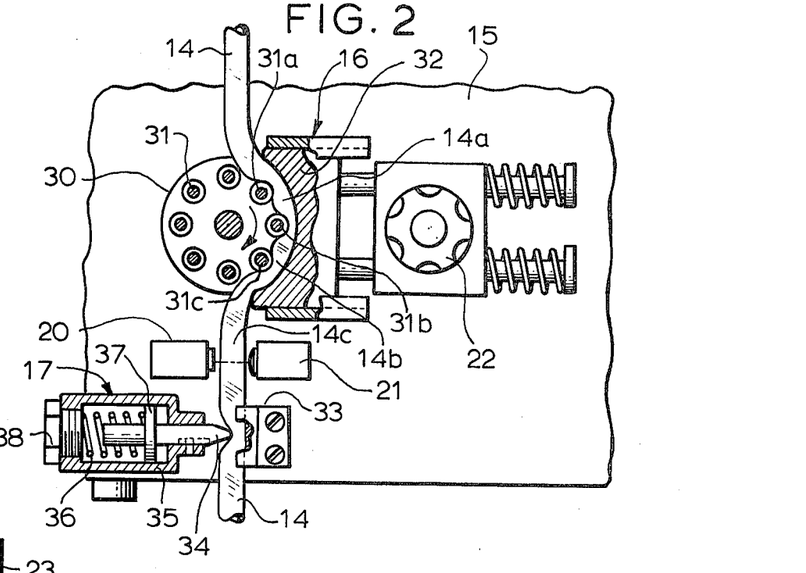
FIG. 2 is an enlarged front elevational view of the peristaltic pump and flow restriction station of the infusion system shown in FIG. 1.

Referring to FIG. 2, the peristaltic pump 16 includes a rotor 30 having a plurality of pressure rollers 31 disposed in equi-spaced relationship about its circumference. A pressure block 32 having a working surface substantially corresponding in shape to the circumference of the pump rotor 30 is positioned to bring the tubing 14 into pressure engagement with a portion of the rollers 31 such that as rotor 30 turns (clockwise in FIG. 2) the rollers allow fluid contained in the lumen of the tubing to pass through the tubing toward the needle adaptor. In FIG. 2 the three rollers 31a, 31b and 31c in engagement with conduit 14 form two isolated segments 14a and 14b along the tubing in which the fluid is contained as it flows downline. It will be noted that the tubing 14 must be substantially completely compressed under the rollers and at least partially restored to its normal uncompressed state between the rollers in order for the peristaltic pump to function.

After passing through the peristaltic pump, tubing 14 extends between light source 20 and photodetector 21 to the flow restriction station. This stage includes a pressure block 33 and a slidably mounted wedge-shaped plunger 34 which bears against the wall of the tubing as it is held in position against the pressure block. As a result, the lumen of the tubing is reduced to form a conduit segment 14c between the point of engagement of the last roller 31 of the pump and the point of engagement of the wedge-shaped plunger 34. The piston 14 is slidably mounted within a housing 35 and is biased against the wall of tubing 34 by means of a helical spring 36 within the housing which bears against a collar 37 attached to the plunger and a cap 38 removably threaded into the rear of the housing.

Figure 3A:
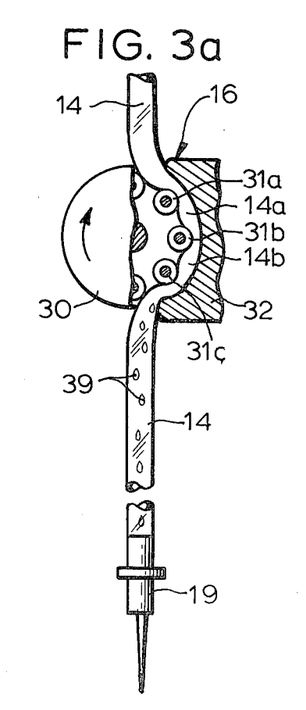
FIGS. 3a and 3b are enlarged views of a portion of the infusion system illustrating the effect of the flow restriction station on the system.
Figure 3B:
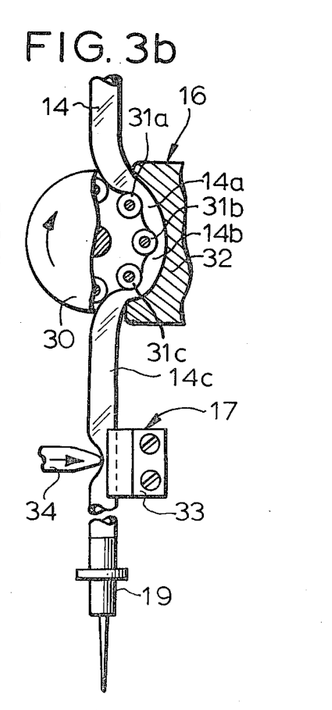

In accordance with one aspect of the invention, flow restriction station 17 functions to increase the pressure in tubing section 14c. As shown in FIG. 3a, absent this flow restriction station dissolved gases in the fluid being administered could separate from the fluid downline of the pump station as a result of temperature and/or pressure changes brought about by the action of the pump rollers 31 or as a result of the fluid being heated by the pump assembly at low flow rates, forming bubbles 39 between the needle adaptor 19 and the pump station. These bubbles if allowed to coalesce could form air pockets which, if infused, could result in death or serious injury to a patient. As shown in FIG. 3b, with the flow restriction stage the pressure on the fluid in conduit 14c is increased and separation of the dissolved gases is prevented.

Also, in further accord with the invention, the pressure in segment 14c assists in expanding the walls of the tubing after the last pressure roller 31 has become disengaged from the tubing. This is illustrated in FIG. 3b, wherein roller 31c is about to disengage from the tubing and the pressure developed in segment 14c is about to assist in reforming the outer wall of the tubing to allow free passage of the fluid trapped in pocket 14b away from the pump station. It is this restoration force on the walls of the tubing which enables a peristaltic-type pump to be used in conjunction with the vinyl or thermoplastic tubing commonly employed in fluid administration sets.

The same principles apply when utilizing a linear-type peristaltic pump, which can be substituted for the rotary-type peristaltic pump shown in FIGS. 1-3. In this instance, tubing 14 is routed over a pressure block 41 and a plurality of individually extensible fingers 42 are brought to bear against the wall of the tubing. The fingers 42 compress tubing 14 in at least two separate locations 14d and 14e so as to form an isolated uncompressed tubing section 14f. In operation the fingers are extended cyclically from left to right so as to move the isolated segment 14f, and hence the fluid trapped therein, downline from the pump. The system includes a fluid flow restriction station 17 downline of pump 40 which may be identical to its counterpart in the previously described pump assembly 15. This forms a tubing segment 14g within which the fluid pressure is increased to prevent the separation of dissolved gases from the fluid and to assist in reformation of the tubing following compression by the fingers of the peristaltic pump 40.

Figure 4:
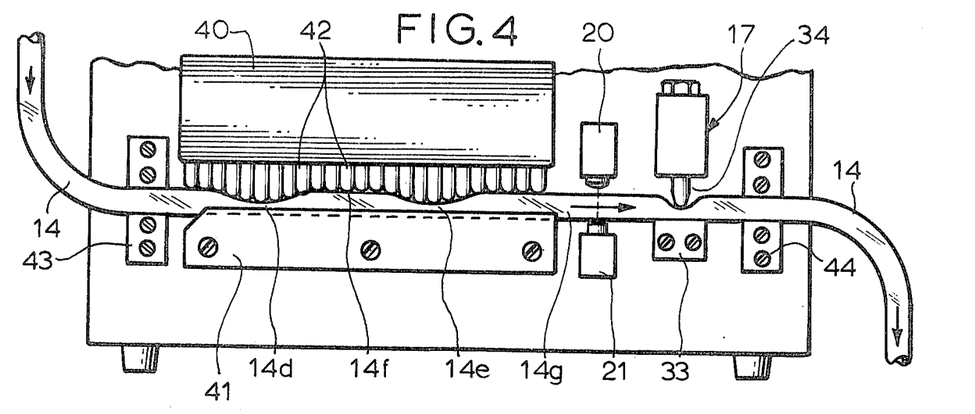
FIG. 4 is a front elevational view of a linear-type peristaltic pump and associated flow restriction station suitable for use in conjunction with the infusion system shown in FIG. 1.

To assist in maintaining tubing 14 in alignment, the pump apparatus shown in FIG. 4 may include a first tubing retaining member 43 upline of pump 40 and a second tubing retaining member 44 downline of restricting station 17. As in the previously described pump apparatus 15, a light source 20 and a photodetector 21 may be provided in connection with tubing segment 14g to detect the absence of fluid in the system.

Figure 5:
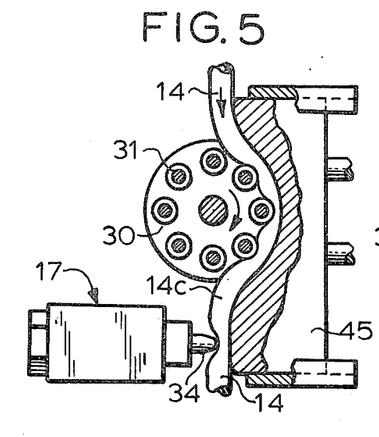
FIG. 5 is an enlarged view of a rotary-type peristaltic pump and associated flow restriction station utilizing a common support block.

It will be appreciated that various modifications can be made to the structure of the pump assembly 15 of the infusion system 10 for improved ease of operation. For example, as shown in FIG. 5 a common pressure block can be utilized for both the peristaltic pump and flow restriction stations. The pressure block 45 includes a curved portion which, like its counterpart 32 in FIG. 2, causes the tubing 14 to bear against the pressure rollers 31 of the pump rotor 30. The pressure block includes a flat portion downline of the rotor to provide a surface against which plunger 34 can bear. This arrangement simplifies the installation and removal of tubing 14, but requires other flow restrictive means (such as closure of clamp 18) to prevent gravity flow if block 45 fails or is disengaged.

Figure 6:
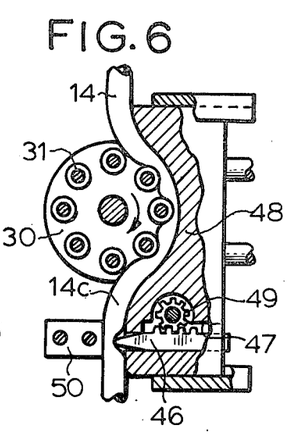
FIG. 6 is an enlarged front elevational view of a rotary-type peristaltic pump similar to that shown in FIG. 5 showing an alternate construction for the flow restriction station.

A modification of the common pressure block arrangement shown in FIG. 5 is shown in FIG. 6. In this embodiment the flow restriction station consists of a wedge-shaped plunger 46 slidably mounted within a channel 47 provided in a pressure block 48. The wedge-shaped end of the plunger 46 bears against a stationary pressure block 50 to restrict the lumen of tubing 14. A user-rotatable cog 49 engaging a toothed rack surface on the plunger enables the plunger to be selectively extended or retracted by the user to vary the pressure exerted on the tubing to accommodate tubing having various diameters and wall thicknesses as well as to compensate for various temperature and pressure effects which may be encountered.

Figures 7, 9:
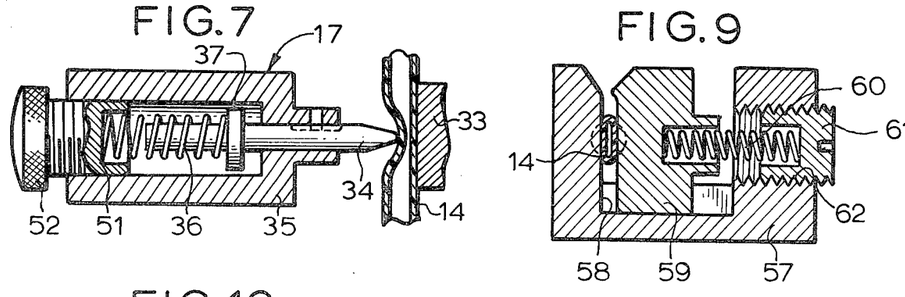
FIG. 7 is an enlarged front elevational view partially in cross-section showing the details of the construction of the flow restriction station shown in FIG. 2.
FIG. 9 is a front elevational view of another alternate construction for the flow restriction station.

Referring to FIG. 7, a similar pressure adjustment is accomplished in the flow restriction station 17 shown in FIGS. 1 and 2 by providing an adjustable cap member 51 at the rear of spring 36 so that the force exerted by the spring, and hence the force exerted by the plunger, can be increased or decreased by the user. The cap member is threaded into housing 35 and may include a knurled knob portion 52 which can be grasped by the user to facilitate turning the cap with respect to the housing.

Figure 8:
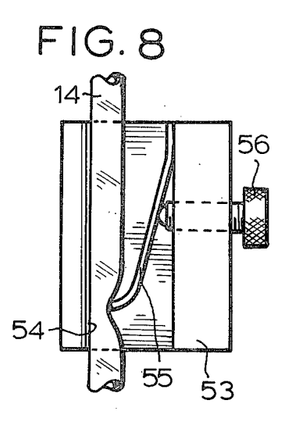
FIG. 8 is a front elevational view of an alternate construction for the flow restriction station.

Still another form which the flow restriction station can take is shown in FIG. 8. In this embodiment a pressure block 53 is provided having a channel 54. Tubing 14 is seated along one wall of this channel and flat spring member 55 is attached to the opposite wall of the channel. The spring member is brought to bear against the wall of the tubing by means of a threaded thumb screw 56 which bears against the central portion of the spring member to extend its free end toward the tubing.

Another construction for the flow restriction station is shown in FIG. 9. In this embodiment a pressure block 57 is provided having a central channel 58 in which a second pressure block 59 is slidably disposed. The tubing 14 is positioned between the stationary block 57 and the slidable block 59 and the two blocks are brought together by means of a spring 60 working against a user-adjustable slug member 61 threaded into a bore 62 in block 57.

Figure 10:
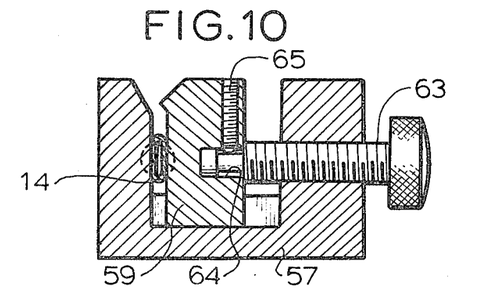
FIG. 10 is a front elevational view partially in cross-section of another alternate embodiment for the flow restriction station.

A modification of this arrangement is shown in FIG. 10. In this embodiment the slidably mounted pressure block 59 is urged against tubing 14 by means of a thumb screw 63 which is threaded into the stationary block 57 and seated in a bore 64 provided in block 59. A set screw 65 couples thumb screw 63 to block 59 for axial movement but not for rotational movement.

While the flow restriction station need comprise only a fixed pressure block against which a fixed plunger is brought to bear, substantial benefits result from spring loading the plunger. Such spring loading obviates the need for adjusting the flow restriction to accommodate different flow rates and different sizes of tubing. Also, the provision of a spring loaded plunger allows the tubing to be completely blocked off in the absence of pressure from the pump so that in the event of the pump failing or being inadvertently removed the plunger operates to completely pinch off the conduit and prevent uncontrolled gravity flow into the patient. Furthermore the spring loading assists in maintaining a constant upline pressure in the tubing as the downline roller disengages from the tubing.

By reason of the capability of peristaltic pumps to generate relatively large flow pressure, a relatively large force can be exerted by the plunger of the flow restriction station on tubing 14 to ensure that in the absence of pressure from the pump the conduit will be completely crimped shut. In one successful embodiment of the invention utilizing a rotary-type peristaltic pump, vinyl tubing having a wall thickness of 0.022 inch and a lumen of 0.100 inch diameter was subjected to a pressure of 100 pounds.

Prior to use, the peristaltic pump is opened and the tubing of the solution administration set is routed from the reservoir through the pump and the flow restriction station to the patient. The pump is then operated until tubing 14 has filled with fluid. The needle is now inserted into a vein or artery and the pump is again placed in operation to begin controlled infusion of the fluid into the patient. The rate of infusion is set by means of controls provided on the pump assembly. The administration set can also be filled from the reservoir by gravity means prior to placement of the tubing in the pump, with patient attachment following or just prior to tubing placement in the pump. In either case, the restriction in the tubing lumen introduced by the flow restriction station downline of the pump station generates a back pressure against which the pump must work. This prevents the separation of gases dissolved in the fluid as the temperature and/or pressure of the fluid are changed as a result of the action of the pump. The flow restriction also serves to prevent free gravity flow of fluid through the system in the absence of system pressure.

The downline flow restriction stage contemplated by the invention may be more advantageously employed where the rotor has a lesser number of pressure rollers, such as in the four roller embodiment shown in FIGS. 11–15.

In this embodiment, the peristaltic pump includes a rotor 70 having four pressure rollers 71 disposed in equispaced relation about its circumference. The rollers are each mounted on a shaft 72 for free rotation thereon, and the shafts are carried on a carriage 73 (FIG. 14) and constrained to radial movement by a respective radial slot 74. Each carriage 73 is mounted for reciprocation within a radially aligned sleeve 75 and spring loaded in a radially outward direction by a helical spring 76 disposed within the sleeve. The spring is seated at one end within a recess 77 on the carriage and at its other end within a recess 78 provided on the hub of the rotor.

Figure 14:
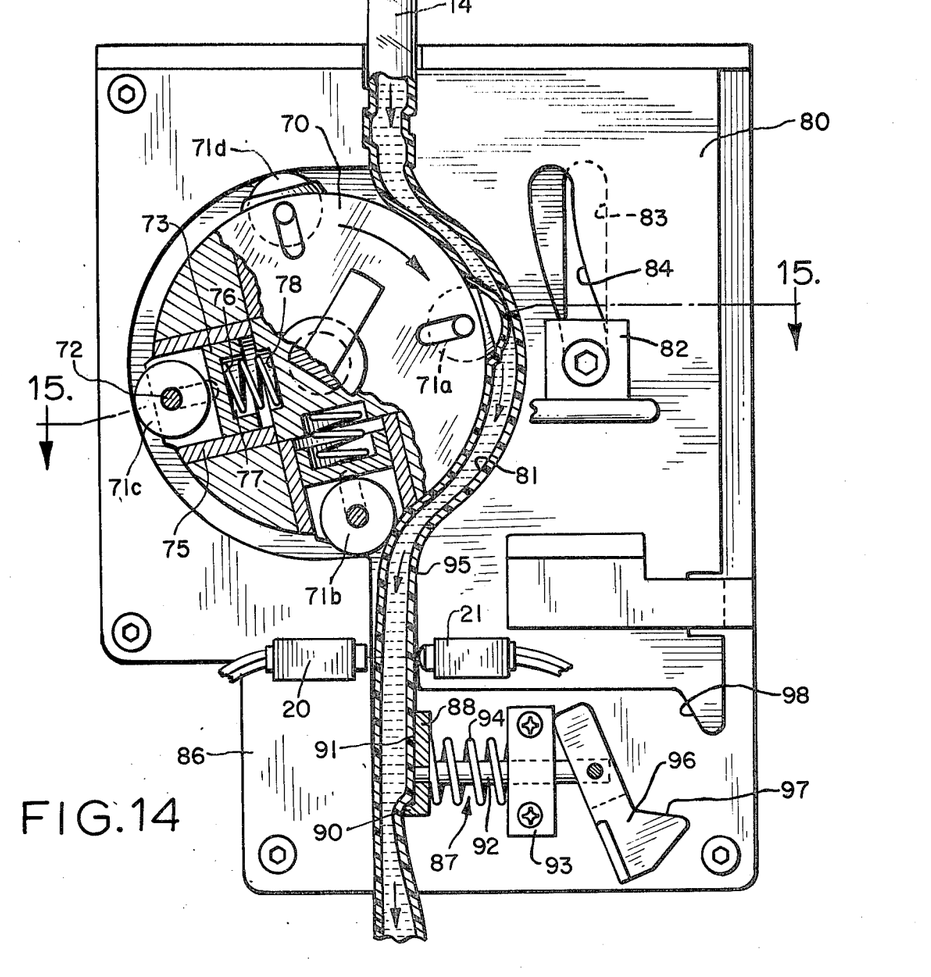
FIG. 14 is a front elevational view of the peristaltic pump in a closed operating state partially broken away to show the construction of the pressure rollers provided within the pump rotor.
Figure 15:
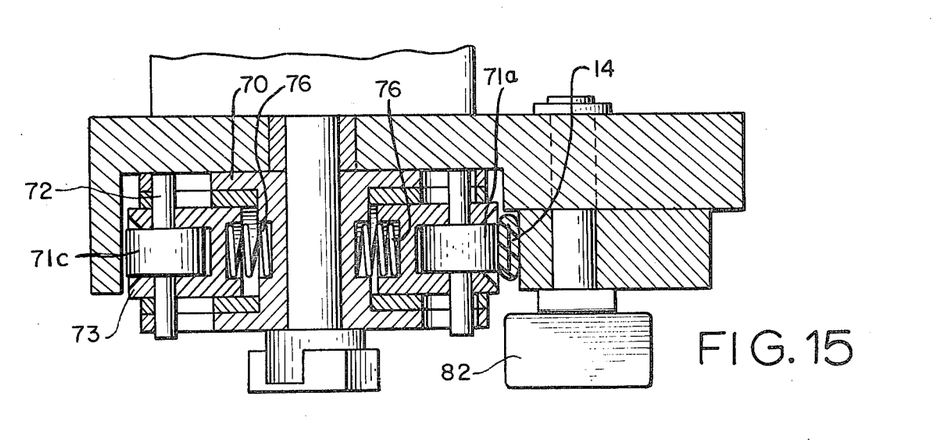
FIG. 15 is a cross-sectional view of the peristaltic pump taken along line 15—15 of FIG. 14.

The pump also includes a pressure plate 80 having an arcuate working surface 81 which substantially corresponds in shape to the circumference of the pump rotor 70 and is positioned to bring tubing 14 into compressive engagement with a portion of the rollers 71 around at least that portion of the rotor circumference extending between adjacent rollers. For the four roller embodiment illustrated, at least a 90° portion of the tubing 14 must extend around the rotor circumference. The pressure plate may be reciprocated toward and away from rotor 70 to facilitate installation and removal of tubing segment 14 by movement of lever 82, which is constrained within a vertical slot 83 provided on the pump frame. This motion is converted to transverse motion of the pressure plate by a cam carried on lever 82 which engages a transversely progressive slot 84 on the pressure plate. When the lever 82 is in its bottom position, as shown in FIG. 14, the pressure plate is moved toward roller 70 with its work surface 81 sufficiently close to the rotor circumference to cause tubing 14 to be completely occluded by the rollers. In this position, it will be noted that the pressure plate is locked in position and held stationary with respect to the rotor. Since each roller 71 is individually biased into engagement with the tubing segment, the pressure applied is independent of the position of the roller and of the number of rollers engaging the tubing segment.

As in the previous embodiments, after passing through the peristaltic pump, tubing 14 extends between a light source 20 and a photodetector 21, which together comprise a gas or bubble detector, to a flow restriction station. This station includes a pressure block 86 and a slidably mounted flow restriction plunger 87. In accordance with another aspect of the invention, the end of plunger 87 which engages tubing 14 includes a generally L-shaped head portion 88 defining a wedge-shaped working surface 90 and a flat control surface 91. Plunger 87 includes a shaft portion 92 which is slidably received by a mounting block 93, and which extends through the center of a helical compression spring 94 provided for biasing head 88 into engagement with tubing 14.

The working surface 90 bears against the sidewall of tubing 14 substantially perpendicular to the direction of fluid flow within the tubing as the tubing is held in position against pressure block 86. As a result, the lumen of the tubing is occluded at the point of engagement, and a downline conduit segment 95 is defined between the point of engagement of the roller 71a (FIG. 14) of the pump and the point of engagement of the working surface 90. As previously developed, the occlusion of the tubing increases the pressure of the fluid in segment 95 and prevents separation of dissolved gases therein. Since the four rollers 71 provided have a separation about the circumference of rotor 70 which corresponds to slightly less than that portion of the circumference engaged by tubing segment 14, as contemplated by another aspect of the invention, substantially the entire tubing segment downline of the flow controlling roller 71a (FIG. 14) is subjected to back pressure. This provides optimum pump operation, since back pressure is available over the entire length of the tubing on which the pump rollers act, thus preventing gas separation in the isolated tubing sections which would otherwise exist were a larger portion of the rotor circumference and a corresponding larger number of rollers to be engaged by the tubing. This also eliminates metering inaccuracies which might result from portions of the tubing segment being acted upon not receiving a restoring force following roller engagement, since over a period of time such isolated tubing portions would not completely restore to this uncompressed shape due to cold flow and other fatigue, time and temperature related phenomena.

In accordance with another aspect of the invention, the control surface 91 of plunger 87 extends substantially parallel to the direction of fluid flow and is substantially greater in area than the control surface 91. The relatively large area of the working surface 90 renders the plunger more sensitive to pressures in the tubing lumen when the pump is operative so that higher pressures can be exerted by spring 94 to more positively close off the tubing when the pump is not in operation, without detriment to its ability to open even at lower operating pressures. As a result, the pump of the present invention provides improved performance with vinyl and other thermoplastic tubing.

As a specific example of the improved performance obtainable by employing the control surface, for typical vinyl tubing with a lumen of 0.100 inch and a wall thickness of 0.020 inch occluded by a plunger having a spring force of 3.5 lbs. and an effective working surface area of 0.014 sq. inch, a fluid pressure of up to 250 P.S.I. would have to be developed by the pump to open the occlusion. However by providing a control surface having an effective tubing land area of 0.042 sq. inch, only 83 P.S.I. would be required to open the plunger.

Figure 11:
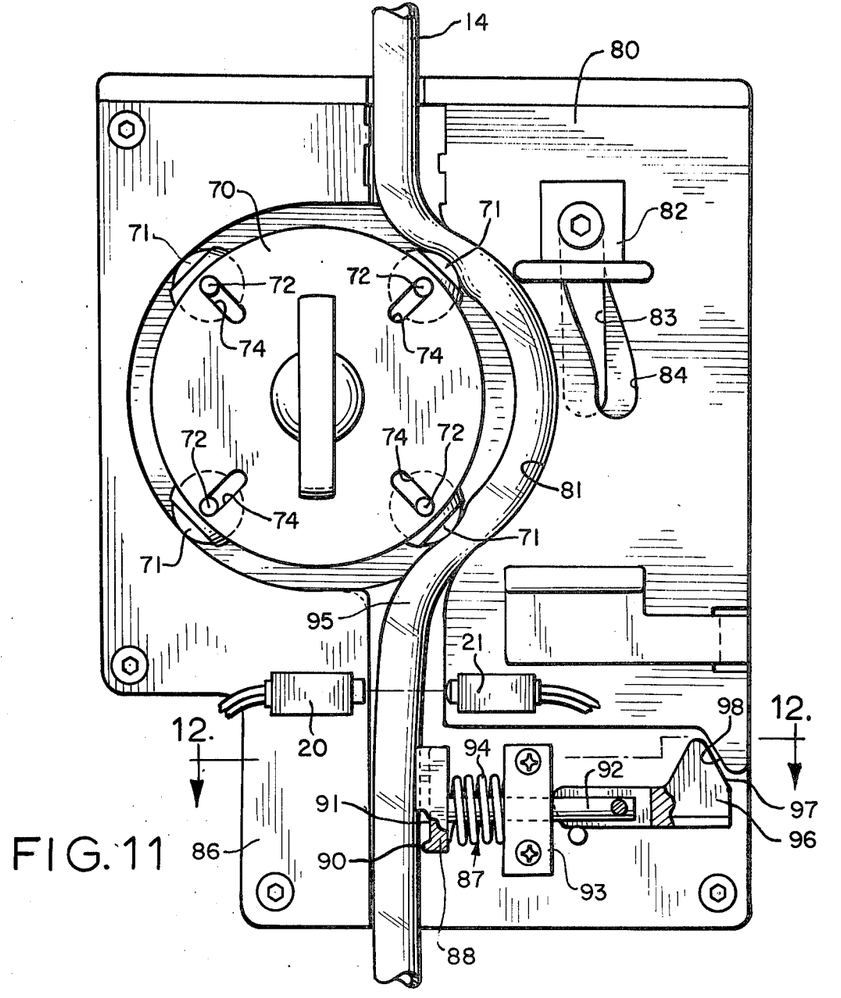
FIG. 11 is a front elevational view of a peristaltic pump constructed in accordance with the invention in a non-operating open state.

Plunger 87 may be conditioned open to facilitate loading or unloading tubing setment 14 by means of a useractuated lever 96 pivotally attached to the free end of stem 92. In the open position of the plunger, as shown in FIG. 11, lever 96 is positioned over-center with respect to the stem, thereby locking the flow restriction plunger open. In the closed position, as shown in FIG. 14, the lever is repositioned so as to allow free movement of the stem. A camming surface 97 on the lever cooperates with a camming surface 98 on pressure plate 80 to automatically close plunger 87 upon closure of the pressure plate.

Figure 12:
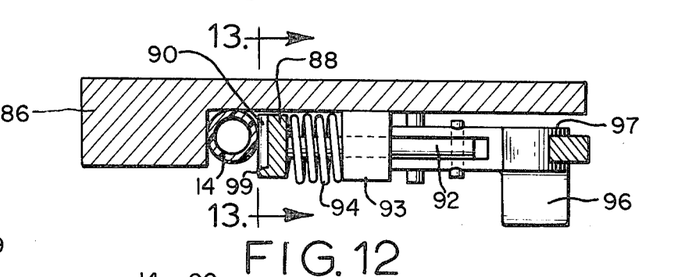
FIG. 12 is a cross-sectional view of the peristaltic pump taken along line 12—12 of FIG. 11 showing the flow restriction station therein conditioned open.
Figure 12A:
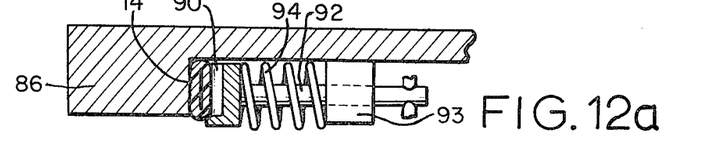
FIG. 12a is a cross-sectional view as above showing the flow restriction station conditioned closed.

When closed the pressure exerted by spring 94 is sufficient to completely occlude tubing 14 in the absence of pressure from the pump, as shown in FIG. 12a. However, during operation sufficient pressure is developed within the lumen of the tubing to at least partially open the tubing, as shown in FIG. 14. This pressure exists within the entire tubing segment 95, and serves to prevent the sudden changes in fluid pressure which would otherwise occur in the segment as the downline roller (71b in FIG. 14) disengages from the tubing.

Figure 13:
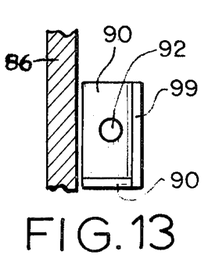
FIG. 13 is a cross-sectional view taken along line 13—13 of FIG. 12 showing the control and working surfaces of the flow restriction plunger.

As best shown in FIG. 13, the head 88 of plunger 87 preferably includes a gate member 99 which prevents tubing 14 from being disengaged.

While particular embodiments of the invention have been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

I claim:

1. A flow system for infusing a fluid from a supply reservoir into the human body, comprising, in combination:
   a length of flexible-walled tubing extending from the supply reservoir to the body, said tubing exhibiting incomplete restoration upon repeated compressive cycling thereof;
   means continuously including at least one pressure means compressively engaged to the sidewall of said tubing for completely occluding the lumen thereof;
   means for advancing the point of engagement of said pressure means along a segment of said tubing, the lumen of said tubing being repetitively and progressively compressed and restored along said segment to urge fluid through said tubing; and
   flow restriction means for continuously at least partially restricting the lumen of said tubing downline of said tubing segment to increase the pressure of the fluid within said segment downline of said point of engagement to assist in reformation of said tubing for improved metering accuracy.

2. A flow system as defined in claim 1 wherein said flow restriction means comprise a movable plunger spring-biased against the wall of said tubing.

3. A flow system as defined in claim 2 wherein said plunger bears against said wall of said tubing with a force sufficient to prevent flow of fluid through said tubing when said pressure means is stationary.

4. A flow system as defined in claim 3 wherein said plunger has a wedge-shaped working surface of relatively small area bearing against said tubing generally perpendicular to the direction of flow therein, and a control surface of relatively larger area extending substantially parallel to the direction of flow therein and upline from said working surface for responding to pressure changes in said tubing.

5. A flow system as defined in claim 1 wherein said tubing is formed of vinyl.

6. A flow system as defined in claim 1 wherein said fluid is subject to pressure changes as a result of said repetitive compression and expansion giving rise to separation of gas from said fluid, and wherein detector means for detecting the presence of undissolved gas in the lumen of said tubing are provided downline of said tubing segment and upline of said flow restriction means, the increased pressure of said fluid therein maintaining said gas in solution and preventing actuation of said detector means by said gas.

7. A flow system for infusing a fluid from a supply reservoir into the human body, comprising, in combination:
   a length of flexible-walled tubing extending from the supply reservoir to the body, said tubing exhibiting incomplete restoration upon repeated compressive cycling thereof;
   means including a rotor having along its circumference a plurality of pressure members, at all times at least one of said pressure members being in compressive engagement with the sidewall of said tubing and completely occluding the lumen thereof;
   means including a pressure plate for bringing said tubing into compressive engagement with said one of said pressure members;
   means for rotatably driving said rotor whereby the lumen of said tubing is repetitively and progressively compressed and restored along said segment to urge fluid through said tubing; and
   flow restriction means for continuously at least partially restricting the lumen of said tubing downline of said tubing segment to increase the pressure of the fluid within said segment downline of said point of engagement of said pressure member to assist in reformation of said tubing for improved metering accuracy.

8. A flow system as defined in claim 7 wherein said pressure members are disposed in equispaced relationship on the circumference of said rotor, and said pressure plate brings said tubing into engagement with said pressure member only over a segment of said tubing substantially corresponding to the spacing of said pressure members on the circumference of said rotor.

9. A flow system as defined in claim 7 wherein said flow restriction means comprise a movable plunger spring-biased against the wall of said tubing.

10. A flow system as defined in claim 9 wherein said plunger bears against said wall of said tubing with a force sufficient to prevent flow of fluid through said tubing when said pressure member is stationary.

11. A flow system as defined in claim 10 wherein said plunger has a wedge-shaped working surface of relatively small area bearing against said tubing generally perpendicular to the direction of flow therein, and a control surface of relatively larger area extending substantilly parallel to the direction of flow therein and upline from said working surface for responding to pressure changes in said tubing.

12. A flow system as defined in claim 7 wherein said tubing is formed of vinyl.

13. A flow system as defined in claim 7 wherein said fluid is subject to pressure changes as a result of said repetitive compression and expansion giving rise to separation of gas from said fluid, and wherein detector means for detecting the presence of undissolved gas in the lumen of said tubing are provided downline of said tubing segment and upline of said flow restriction means, the increased pressure of said fluid therein maintaining said gas in solution and preventing actuation of said detector means by said gas.

14. Metering apparatus for infusing a fluid from a supply reservoir to the human body through a length of flexible-walled tubing of the type exhibiting incomplete restoration upon repeated compressive cycling thereof, comprising, in combination:
   means continuously including at least one pressure means compressively engaged to the sidewall of the tubing for completely occluding the lumen thereof;
   means for advancing the point of engagement of said pressure means along a segment of the tubing, the lumen of the tubing being repetitively and progressively compressed and restored along said segment to urge fluid through the tubing; and
   flow restriction means for continuously at least partially restricting the lumen of the tubing downline of said tubing segment to increase the pressure of the fluid within said segment downline of said point of engagement to assist in reformation of the tubing for improved metering accuracy.

15. Metering apparatus as defined in claim 14 wherein said flow restriction means comprise a movable plunger spring-biased against the wall of the tubing.

16. Metering apparatus as defined in claim 15 wherein said plunger bears against said wall of the tubing with a force sufficient to prevent flow of fluid through the tubing when said pressure means in stationary.

17. Metering apparatus as defined in claim 16 wherein said plunger has a wedge-shaped working surface of relatively small area bearing against the tubing generally perpendicular to the direction of flow therein, and a control surface of relatively larger area extending substantially parallel to the direction of flow therein and upline from said working surface for responding to pressure changes in the tubing.

18. Metering apparatus as defined in claim 14 wherein the tubing is formed of vinyl.

19. Metering apparatus as defined in claim 14 wherein said fluid is subject to pressure changes as a result of said repetitive compression and expansion giving rise to separation of gas from said fluid, and wherein detector means for detecting the presence of undissolved gas in the lumen of said tubing are provided downline of said tubing segment and upline of said flow restriction means, the increased pressure of said fluid therein maintaining said gas in solution and preventing actuation of said detector means by said gas.

20. Metering apparatus for infusing a fluid from a supply reservoir to the human body through a length of flexible-walled fubing of the type exhibiting incomplete restoration upon repeated compressive cycling thereof; comprising;
   means including a rotor having along its circumference a plurality of pressure members, at all times at least one of said pressure members being in compresive engagement with the sidewall of the tubing and completely occluding the lumen thereof;
   means including a pressure plate for bringing the tubing into compressive engagement with said one of said pressure members along a segment of said tubing;
   means for rotatably driving said rotor whereby the lumen of the tubing is repetitively and progressively compressed and restored along said segment to urge fluid through the tubing; and
   flow control means for continuously at least partially restricting the lumen of the tubing downline of said tubing segment to increase the pressure of the fluid within said segment to increase the pressure of the fluid within said segment downline of point of engagement of said pressure member to assist in reformation of the tubing for improved metering accuracy.

21. Metering apparatus as defined in claim 20 wherein said pressure members are disposed in equi-spaced relationship on the circumference of said rotor and said pressure plate brings said tubing into engagement with said pressure member only over a segment of said tubing substantially corresponding to the spacing of said pressure members on the circumference of said rotor.

22. Metering apparatus as defined in claim 20 wherein said flow restriction means comprise a movable plunger spring-biased against the wall of the tubing.

23. Metering apparatus as defined in claim 22 wherein said plunger bears against said wall of the tubing with a force sufficient to prevent flow of fluid through the tubing when said pressure member is stationary.

24. Metering apparatus as defined in claim 23 wherein said plunger has a wedge-shaped working surface of relatively small area bearing against the tubing generally perpendicular to the direction of flow therein, and a control surface of relatively larger area extending substantially parallel to the direction of flow therein and upline from said working surface for responding to pressure changes in the tubing.

25. Metering apparatus as defined in claim 20 wherein the tubing is formed of vinyl.

26. Metering apparatus as defined in claim 20 wherein said fluid is subject to pressure changes as a result of said repetitive compression and expansion giving rise to separation of gas from said fluid, and wherein detector means for detecting the presence of undissolved gas in the lumen of said tubing are provided downline of said tubing segment and upline of said flow restriction means, the increased pressure of said fluid therein maintaining said gas in solution and preventing actuation of said detector means by said gas.

27. Metering apparatus for infusing a fluid from a supply reservoir to the human body through a length of flexible-walled tubing of the type exhibiting incomplete restoration upon repeated compressive cycling thereof, comprising, in combination:
   means including a rotor having in equi-spaced relationship along its circumference a plurality of pressure members, at all times at least one of said pressure members being in compressive engagement with the sidewall of said tubing and completely occluding the lumen thereof;

means including a pressure plate for bringing said tubing into compressive engagement with said one of said pressure members only over a segment of said tubing substantially corresponding to the spacing of said pressure members on the curcumference of said rotor;

means for rotatably driving said rotor whereby the lumen of said tubing is repetitively and progressively compressed and restored along said segment to urge fluid through said tubing;

detector means downline of said tubing segment and upline of said flow restriction means for detecting the presence of undissolved gas in the lumen of said tubing; and flow restriction means comprising a movable plunger spring-biased against the wall of said tubing, and having a wedge-shaped working surface of relatively small area bearing against said tubing generally perpendicular to the direction of flow therein, and a control surface of relatively larger area extending substantially parallel to the direction of flow therein and upline from said working surface for responding to pressure changes in said tubing, for continuously at least partially restricting the lumen of said tubing downline of said tubing segment to increase the pressure of the fluid within said segment downline of said point of engagement of said pressure member to assist in reformation of said tubing for improved metering accuracy.

28. The method of infusing a fluid from a supply reservoir into the human body, comprising the steps of:

establishing a flow path between the supply reservoir and the human body through a length of flexible-walled tubing of the type exhibiting incomplete restoration upon repeated compressive cycling thereof;

continuously compressing the sidewall of said tubing so as to completely occlude said tubing;

repetitively advancing the point of compression of said tubing along a segment thereof whereby the lumen of said tubing is repetitively and progressively compressed and restored along said segment to urge fluid through said tubing; and at least partially restricting the lumen of said tubing downline of said tubing segment to increase the pressure of the fluid within said segment downline of said point of compression to assist in reformation of said tubing segment improved metering accuracy.

29. The method of infusing fluid as defined in claim 28 wherein the flow path is established through flexible-walled vinyl tubing.

* * * * *

UNITED STATES PATENT AND TRADEMARK OFFICE
CERTIFICATE OF CORRECTION

PATENT NO. : 4,155,362
DATED : May 22, 1979
INVENTOR(S) : Thurman S. Jess

It is certified that error appears in the above-identified patent and that said Letters Patent are hereby corrected as shown below:

In Column 11, Line 48, after "means" delete "in" and insert -- is --.

In Column 12, Lines 22-23, after "segment" delete -- to increase the pressure of the fluid within said segment -- .

Signed and Sealed this

Twenty-eighth Day of August 1979

[SEAL]

Attest:

*Attesting Officer*

LUTRELLE F. PARKER
*Acting Commissioner of Patents and Trademarks*